U.S. Patent Number: 5,493,061
Date of Patent: Feb. 20, 1996

[54] PROCESS FOR THE CONVERSION OF PHENOL TO HYDROQUINONE AND CATECHOL

[75] Inventors: Paul Ratnasamy; Subramanian Sivasanker, both of Pune, Ind.

[73] Assignee: Council of Scientific & Industrial Research, New Delhi, Ind.

[21] Appl. No.: 353,819

[22] Filed: Dec. 9, 1994

[51] Int. Cl.⁶ ............................. C07C 37/60; C07C 37/00
[52] U.S. Cl. .............................................. 568/771; 568/803
[58] Field of Search ...................................... 568/771, 803

[56] References Cited

U.S. PATENT DOCUMENTS

| | | | |
|---|---|---|---|
| 3,329,482 | 7/1967 | Young | 423/326 |
| 3,920,756 | 11/1975 | Tahara et al. | 568/771 |
| 3,929,913 | 12/1975 | Maggioni | 568/771 |
| 3,941,871 | 3/1976 | Dwyer et al. | 423/326 |
| 4,396,783 | 8/1983 | Esposito et al. | 568/771 |
| 4,954,653 | 9/1990 | Bellussi et al. | 564/223 |
| 5,233,097 | 8/1993 | Nemeth et al. | 568/803 |
| 5,254,746 | 10/1993 | Costantini et al. | 568/624 |
| 5,426,244 | 6/1995 | Sugai et al. | 568/771 |

*Primary Examiner*—Werren B. Lone
*Attorney, Agent, or Firm*—Schweitzer Cornman & Gross

[57] ABSTRACT

This invention relates to a process for the oxidation of phenol to a mixture of hydroquinone and catechol using hydrogen peroxide as oxidant in the presence of titanium silicate molecular sieves in a multistage fixed bed reactor.

6 Claims, No Drawings

PROCESS FOR THE CONVERSION OF PHENOL TO HYDROQUINONE AND CATECHOL

BACKGROUND AND SUMMARY OF THE INVENTION

This invention relates to an improved process for the conversion of phenol to a mixture of hydroquinone and catechol. More particularly this invention relates to a process for the oxidation of phenol to a mixture of hydroquinone and catechol using hydrogen peroxide as the oxidant in the presence of titanium silicate molecular sieves in a multistage fixed bed reactor.

Many processes are known in the prior art for the conversion of phenol to hydroquinone and catechol using hydrogen peroxide, $H_2O_2$ as the oxidant. In U.S. Pat. No. 3,929,913, assigned to Brichima, the catalyst used is farrocane, ferrous sulfate chelates are used as catalysts in the U.S. Pat. No. 3,920,756. In the Rhone Poulano process described J. Varagnat in the journal of Industrial Engg. Chemistry, product Research Development, Vol. 15, page 212 (1976), a combination of phosphoric and perchloric acids are used as catalysts. The use of molecular sieves as catalysts for the oxidation of phenol to hydroquinone and catechol using $H_2O_2$ as the oxidant is also known. European Patent 0266825 describes the use of crystalline gallium titanium silicates as catalysts. European Patent 0265018 describes the use, as catalysts, of zeolites with a pore diameter between 5 and 12A. Of more relevance to the present invention, U.S. Pat. No. 4,396,783 and U.K. Patent 2116974 both assigned to Enichem claim the use of a titanium silicate molecular sieve, TS-1, in the hydroxylation of aromatics.

In prior art processes using titanium silicate molecular sieves, as for example, the Enichem process, phenol and $H_2O_2$ in a molar ratio equal to or lower than 5, are contacted at 60°–150° C. with a titanium cilicate molecular sieve containing titanium in a proportion, calculated as $TiO_2$, of between 0.1 and 7% by weight and preferably between 2 and 4% wt. to yield the products hydroquinone and catechol. In addition to the above desired products, significant amounts of heavy oxidation products, hereinafter referred to as tar, were also produced in the process. In example 5 of U.S. Pat. No. 4,396,783, for instance, 21% by weight of phenol was converted into by product tar. The tar originates from the further reaction of hydroquinone and catechol at the elevated temperatures during the exothermic oxidation of phenol. Any modification of the process which reduces the formation of tar will constitute a significant improvement of the process.

It is, therefore, an object of this invention to provide an improved process for the oxidation of phenol to hydroquinone and catechol wherein the production of the undesired by product tar is suppressed leading thereby to enhanced yields of hydroquinone and catechol.

Another object of the present invention is to provide a continuous rather than a batch or semibatch process for the oxidation of phenol. Other and additional objects of this invention will become apparent from a consideration of this entire specification including the claims thereof.

DETAILED DESCRIPTION OF THE INVENTION

Accordingly, the invention provides an improved process for the oxidation of phenol to hydroquinone and catechol which comprises (1) passing at a temperature below 65° C. a mixture of phenol and aqueous hydrogen peroxide, wherein the molar ratio of phenol to hydrogen peroxide is between 10 and 15, through a first reaction zone containing a titanium silicate molecular sieve, the molar ratio of silicon to titanium atoms in the said titanium silicate being less than 50 (2) cooling the effluent from the first reaction zone to below 65° C. and adding aqueous hydrogen peroxide to the said first effluent to bring the molar ratio of phenol to hydrogen peroxide therein to a value between 10 and 15, (3) passing this mixture through a second reaction zone containing a titanium silicate molecular sieve with a molar ratio of silicon to titanium between 50 and 75, (4) cooling the effluent from the second reaction zone to below 65° C. and adding aqueous hydrogen peroxide to the said second effluent to bring the molar ratio of phenol to hydrogen peroxide therein to a value between 10 and 15, (5) passing this mixture through a third reaction zone containing a titanium silicate molecular sieve with a molar ratio of silicon to titanium above 75 and (6) recovering the hydroquinone and catechol from the effluent from the third reactor.

Oxidation catalysts which can be advantageously used in the process of the present invention include the titanium silicate molecular sieves such as those referred to in U.S. Pat. Nos. 4,396,73; 3,329,482; 3,941,871, for example.

As was noted above, as phenol and hydrogen peroxide pass through each oxidation stage, the oxidation reactions taking place increase the reactants' temperature requiring intermediate cooling. The molar composition of phenol to hydrogen peroxide and catalyst composition and especially the molar ratio of silicon and titanium in the titanium silicate catalyst in each stage is, in fact, to some extent dictated by this exothermicity.

It was noted during the course of developing the process of the present invention that the concentration of hydrogen peroxide in the reaction mixture was a major parameter influencing the exothermicity of the reaction process; higher the $H_2O_2$ concentrations of tar. On the other hand, too low concentrations of $H_2O_2$ in the reaction mixture lead to very low concentrations of the dihydroxy benzenes in the product necessitating an inordinate expenditure of energy in the recovery and recycle of the unreacted phenol.

Hence, in one embodiment of the process of the present invention, the molar ratio of phenol to hydrogen peroxide in the reactant mixture is preferably between 10 and 15.

Another factor that influences the formation of tar during the reaction process was found to be the concentration of the oxidation active sites of the oxidation catalyst especially in the downstream portion of the catalyst bed wherein significant quantities of the products dihydroxybenzenes are present. These dihydroxybenzenes are the precursors for the formation of the undesired tar. It may be speculated that these dihydroxy benzenes are oxidised over the oxidation active sites to quinones which undergo further conversion to tar. Hence, while the oxidation active sites are essential in those regions of the catalyst bed wherein the oxidation of phenol is the desired reaction, it is desirable to lower their concentration in those regions of the catalyst bed wherein significant concentrations of the dihydroxybenzenes are present. Accordingly, it is advantageous to have a high concentration of the oxidation active sites in the initial or front end portion of the catalyst bed and a correspondingly lower concentration of the oxidation active sites in the catalyst at the lower end of the catalyst bed. More appropriately, a progressively decreasing concentration of the oxidation active sites in the catalyst bed may be used. More appropriately, a progressively decreasing concentration of the oxidation active sites in the catalyst bed may be used. The oxidation active sites in titanium silicate molecular sieves are the titanium atoms on the surface of the catalyst. The concentration of such titanium atoms may, conveniently be expressed as the molar ratio of silicon to titanium atoms in the solid; higher is this ratio, lower is the titanium content in the solid.

Hence, in another embodiment of the process of the present invention, the molar ratio of silicon to titanium in the titanium silicate molecular sieve varies from below 50 in the initial or front end of the catalyst bed to above 75 toward the final or lower part of the catalyst bed.

While a very large molar ratio of phenol to hydrogen peroxide coupled with a large number of catalytic stage with a progressively increasing silicon to titanium molar ratio in the catalyst bed would have lad to a negligible yield of tar, such an arrangement would be unwieldy in actual practice.

Hence, in another embodiment of the present invention, the oxidation of phenol to the dihydroxybenzenes, hydroquinone and catechol, is carried out preferably in three reaction zones consisting of titanium silicates with three different titanium contents. The molar ratio of silicone to titanium in the titanium silicate molecular sieve catalyst in the first reaction zone is below 50. It is between 50 and 75 in the second reaction zone and above 75 in the third reaction zone. The molar ratio of phenol to hydrogen peroxide remains between 10 and 15 in all the three reaction zones. As mentioned hereinabove, the affluents from each reaction zone is cooled to below 65° C. before they are subsequently introduced along with additional hydrogen peroxide into the next reaction zone.

While the process of the present invention may be practiced using phenol and aqueous $H_2O_2$ in the absence of any solvent, it may, under certain conditions, be preferable to dissolve both phenol and $H_2O_2$ in a solvent and carry out the oxidation reaction. Solvents which may be used advantageously include $H_2O$, acetone, methanol, acetonitrile, t-butanol and dioxane. When such solvents are used the concentration (wt. %) of phenol and $H_2O_2$ in the reaction mixture may vary from 5 to 95% and 5 to 50%, respectively.

It has been found that when the process of conversion of phenol to a mixture of hydroquinone and catechol is carried out in accordance with the above mentioned features and embodiments of this invention, there is a significant reduction in the amount of by-product tar formation.

The following examples are illustrative of the practice of this invention without being limiting on the scope thereof.

EXAMPLE 1

10 g of phenol and 90 g of water ware taken in a three-necked 150 ml flask fitted with a condenser and a thermometer. 1 g of calcined titanium silicate powder with Si/Ti ratio of 33 was added to it. The mixture was heated to 70° C. in an oil bath and 2.78 g of an aqueous solution of $H_2O_2$ (26 wt. %) was added continuously with stirring. The reaction was continued for 6 hours during which the temperature of the reaction mixture was found to increase upto 86° C. and decrease subsequently to the bath temperature. The reaction mixture was analysed with a gas chromatograph. The tar content in the product was estimated by thermogravimetric analysis carried out in an inert gas atmosphere as the weight % of material remaining after the loss of the dihydroxy benzenes.

The product analysis at the end of 6 hours was 7.0% hydroquinone, 4.1% catechol, 0.2% benzoquinone and 1.9% tars.

EXAMPLE 2

10 g of phenol and 90 g of water were taken in a three-necked 150 ml flask fitted with a condenser and a thermometer. 1 g of calcined titanium silicate powder with Si/Ti ratio of 33 was added to it. The mixture was heated to 70° C. in an oil bath and 2.78 g of an aqueous solution of $H_2O_2$ (26 wt. %) was added continuously with stirring. The reaction was continued for 6 hours. The temperature of the reaction mixture was not allowed to increase excessively. The reaction mixture was cooled by immersing a cold finger. By the use of this cooling arrangement, the maximum temperature reached was reduced to 74° C. The product yield was: 7.3% hydroquinone; 4.3% catechol; 0.1% benzoquinone and 1.7% tars.

EXAMPLE 3

The oxidation of phenol was next carried out in a fixed bed reactor as follows: 50 g of the titanium silicate (Si/Ti= 33) catalyst was compacted into pellets (2 mm X 4 mm) and loaded into a 20 mm dia. glass reactor. The reactants, viz., a solution of 10% phenol in water and a solution of 26% $H_2O_2$ in water were passed through a preheater kept at 60° C. at the rate of 100 g and 28 g per hour and then through the catalyst bed; no further heat was supplied to the reactor which was well insulated. The temperature of the different axial zones of the catalyst bed was measured with the help of a moving thermocouple kept inside a thermowell. At steady state conditions, it was noticed that the temperature of the bed increased to 97° C. at a point approximately in the middle of the catalyst bed.

The product was collected for 1 hour and the combined product analysed as before. The product mixture contained 6.8% hydroquinone, 3.8% catechol, no nebzoquinone and 2.9% tars. The larger yield of tars is due to the very high temperature reached inside the reaction zone. The lower yield of hydroquinone and catechol is due to the greater decomposition of hydrogen peroxide at the high temperatures produced inside the reactor.

EXAMPLE 4

The titanium silicate was loaded in a reactor in a 3-bed arrangement such that each bed contained 20 gram of the catalyst and the beds were separated by zones of inert material. The zones were cooled by cooling coils wrapped around them. 120 gm of mixture of phenol and water in the weight ratio of 90:10 and 33.6 gms. of an aqueous solution of hydrogen peroxide (26 wt %) were heated to 60° C. in a preheater and passed through the catalyst beds every hour. The results are given below:

|  | Bed 1 | Bed 2 | Bed 3 |
| --- | --- | --- | --- |
| Inlet temp. | 60° C. | 63° C. | 61° C. |
| Outlet temp. | 78° C. | 74° C. | 65° C. |

The combined product was analysed after one hour of operation. The product mixture contained 8.4% hydroquinone, 5.2% catechol and 1.6% tars.

EXAMPLE 5

The titanium silicate was loaded in a reactor in a 3-bed arrangement such that each bed contained 20 gram of the catalyst and the beds were separated by zones of inert material. The zones were cooled by cooling coils wrapped around them. The temperature at the inlet of each bed was maintained at 62±1°–2° C. with the help of the cooling arrangement. 20 gm of mixture of mixture of phenol and water in the weight ratio of 90.10 was heated in a preheater to 60° C. and passed through the catalyst beds every hour 11.2 gms. of an aqueous solution of hydrogen peroxide (26 wt %) was injected individually at the top of each bed (per hour) without preheating. The phenol water mixture was injected in one lot at the inlet of the first bed. The combined product of one hour had 9.4% hydroquinone; 6.0% catechol and 1.0% tars.

EXAMPLE 6

Titanium silicates with three different titanium contents were loaded in three catalyst beds. The catalyst in the first bed had a Si/Ti ratio of 33, the second bed had a riot of 52, while the third bed had a Si/Ti ratio of 77. The weight of the catalyst in each bed was 20 gms. The beds were separated by zones of inert material. The zones were cooled by cooling coils wrapped around them. The temperature at the inlet of each of each bed was maintained at 62± with the help of the cooling coils. 120 gm of mixture of phenol and water in the weight ratio of 90:10 was heated in a preheater to 60° C. and passed through the catalyst beds every hour 11.2 gms. of an aqueous solution of hydrogen peroxide (26 wt %) without preheating. The phenol water mixture was injected in one lot at the inlet of the first bed. The product composition from the above sequence of beds was found to be as follows: 9.6% hydroquinone; 6.1% catechol and 0.4% tars.

Thus the above examples show that both product yield can be increased and tar formation can be reduced by (1) introduction of $H_2O_2$ in multiple stages and (2) using catalysts with different Si/Ti ratios in different beds.

We claim:

1. An improved process for the oxidation of phenol to form a mixture of hydroquinone and catechol which comprises (1) passing at a temperature below 65° C. a mixture of phenol and aqueous hydrogen peroxide, wherein the molar ratio of phenol to hydrogen peroxide is between 10 and 15, through a first reaction zone containing a titanium silicate molecular sieve, the molar ratio of silicon to titanium atoms in the said titanium silicate being less than 50, (2) cooling the effluent from the first reaction zone to below 65° C. and adding aqueous hydrogen peroxide to the said first effluent to bring the molar ratio of phenol to hydrogen peroxide therein to a value between 10 and 15, (3) passing this mixture through a second reaction zone containing a titanium silicate molecular sieve with a molar ratio of silicone to titanium between 50 and 75, (4) cooling the effluent from the second reaction zone to below 65° C. and adding aqueous hydrogen peroxide to the said second effluent to bring the molar ratio of phenol to hydrogen peroxide therein to a value between 10 and 15, (5) passing this mixture through a third reaction zone containing a titanium silicate molecular sieve with a molar ratio of silicon to titanium above 75 and (6) recovering the hydroquinone and catechol from the effluent from the third reactor.

2. A process as claimed in claim 1, wherein the titanium silicate molecular sieve in the reaction zones 1 to 3 is mixed with an inert binder.

3. A process according to claim 2 wherein the binder is selected from silica, alumina, clays and the like.

4. A process according to claim 1, wherein the content of the titanium silicate is between 20 and 95% wt.

5. A process according to claim 1, wherein a solvent is added to the mixture of phenol and aqueous hydrogen peroxide.

6. A process according to claim 1, wherein the solvent is selected from tertiary butyl alcohol, acetone, water, methanol, acetonitrile and the like and mixture thereof.

* * * * *